(12) United States Patent
Schaefer et al.

(10) Patent No.: US 9,724,181 B2
(45) Date of Patent: Aug. 8, 2017

(54) ORAL CARE IMPLEMENT

(71) Applicant: Braun GmbH, Kronberg (DE)

(72) Inventors: Norbert Schaefer, Frankfurt (DE); Jörn Utsch, Eschborn (DE); Thomas Fritsch, Eppstein (DE)

(73) Assignee: BRAUN GMBH, Kronberg (DE)

( * ) Notice: Subject to any disclaimer, the term of this patent is extended or adjusted under 35 U.S.C. 154(b) by 155 days.

(21) Appl. No.: 14/700,296

(22) Filed: Apr. 30, 2015

(65) Prior Publication Data
US 2015/0320529 A1 Nov. 12, 2015

(30) Foreign Application Priority Data

May 7, 2014 (EP) .................................... 14167339
Apr. 30, 2015 (EP) .................................... 15165850

(51) Int. Cl.
*A61C 17/34* (2006.01)
*A61C 15/04* (2006.01)
(Continued)

(52) U.S. Cl.
CPC ............ *A61C 17/34* (2013.01); *A61C 15/047* (2013.01); *A61C 17/222* (2013.01); *A61C 17/32* (2013.01);
(Continued)

(58) Field of Classification Search
CPC ... A61C 17/222; A61C 17/34; A61C 17/3409; A61C 17/3436; A61C 17/32
See application file for complete search history.

(56) References Cited

U.S. PATENT DOCUMENTS

| | | | | |
|---|---|---|---|---|
| 7,150,061 | B2* | 12/2006 | Kwong | A61C 17/3436 15/22.1 |
| 8,631,532 | B2* | 1/2014 | Utsch | A61C 17/3436 15/22.1 |
| 2010/0269275 | A1* | 10/2010 | Shimoyama | A61C 17/3481 15/22.1 |

FOREIGN PATENT DOCUMENTS

EP     EP 12177800     1/2013

* cited by examiner

*Primary Examiner* — Laura C Guidotti

(57) ABSTRACT

The present disclosure is concerned with an oral hygiene implement having a longitudinal axis, a carrier element mounted for driven movement, a motion transmitter that has a first end for transferring a drive force to the carrier element, which first end is provided at a position being offset from the longitudinal axis, and the motion transmitter has a second end positioned essentially on on the longitudinal axis or is arranged for being positioned essentially on the longitudinal axis during operation, wherein the motion transmitter has a first coupling part comprising the first end, which first coupling part essentially extends along a centre axis arranged at an angle with respect to the longitudinal axis, and a second coupling part comprising the second end, which first coupling part is fixedly connected with a first connecting portion of an elastic pivot element that allows that the first coupling part and the second coupling part can pivot with respect to each other at least in a first pivoting plane spanned by the longitudinal axis and by the centre axis, and wherein the first coupling part is made from a plastics material, including reinforced plastics materials, having a Young's modulus of at least 5000 MPa or from a metal material, and at least the first connecting portion, in particular the whole elastic pivot element, is made from a plastics material having a Young's modulus of not more than (Continued)

3000 MPa, optionally of not more than 1000 MPa, further optionally of not more than 500 MPa.

20 Claims, 5 Drawing Sheets

(51) Int. Cl.
*A61H 13/00* (2006.01)
*A61C 17/22* (2006.01)
*A61C 17/32* (2006.01)
(52) U.S. Cl.
CPC .......... *A61H 13/00* (2013.01); *A61C 17/3436* (2013.01); *Y10T 74/18888* (2015.01)

ORAL CARE IMPLEMENT

FIELD OF THE INVENTION

The present invention is concerned with an oral care implement comprising a motion transmitter coupled with a carrier element mounted for driven movement.

BACKGROUND OF THE INVENTION

It is known that oral hygiene implements such as replacement brush heads for an oral hygiene device such as an electric toothbrush comprise a motion transmitter that is on one end connected with a carrier element such as a brush disc on which cleaning elements such as bristle tufts are mounted and that is on the other end arranged for coupling with a drive shaft of a drive of the handle of the oral hygiene device. European patent application 12177800.5 generally describes such an oral hygiene implement.

It is an object of the present disclosure to provide an oral care implement that is improved over the prior art or that is at least an alternative to the known oral care implements.

SUMMARY OF THE INVENTION

In accordance with one aspect there is provided an an oral hygiene implement having a longitudinal axis, a carrier element mounted for driven movement, a motion transmitter that has a first end for transferring a drive force to the carrier element, which first end is provided at a position being offset from the longitudinal axis, and the motion transmitter has a second end positioned essentially on on the longitudinal axis or is arranged for being positioned essentially on the longitudinal axis during operation, wherein the motion transmitter has a first coupling part comprising the first end, which first coupling part essentially extends along a centre axis arranged at an angle with respect to the longitudinal axis, and a second coupling part comprising the second end, which first coupling part is fixedly connected with a first connecting portion of an elastic pivot element that allows that the first coupling part and the second coupling part can pivot with respect to each other at least in a first pivoting plane spanned by the longitudinal axis and by the centre axis, and wherein the first coupling part is made from a plastics material, including reinforced plastics materials, having a Young's modulus of at least 5000 MPa or from a metal material, and at least the first connecting portion, in particular the whole elastic pivot element, is made from a plastics material having a Young's modulus of not more than 3000 MPa, optionally of not more than 1000 MPa, further optionally of not more than 500 MPa.

BRIEF DESCRIPTION OF THE DRAWINGS

The present disclosure will be further elucidated by a detailed description of example embodiments with reference to figures. In the figures

DETAILED DESCRIPTION OF THE INVENTION

Figure 1:
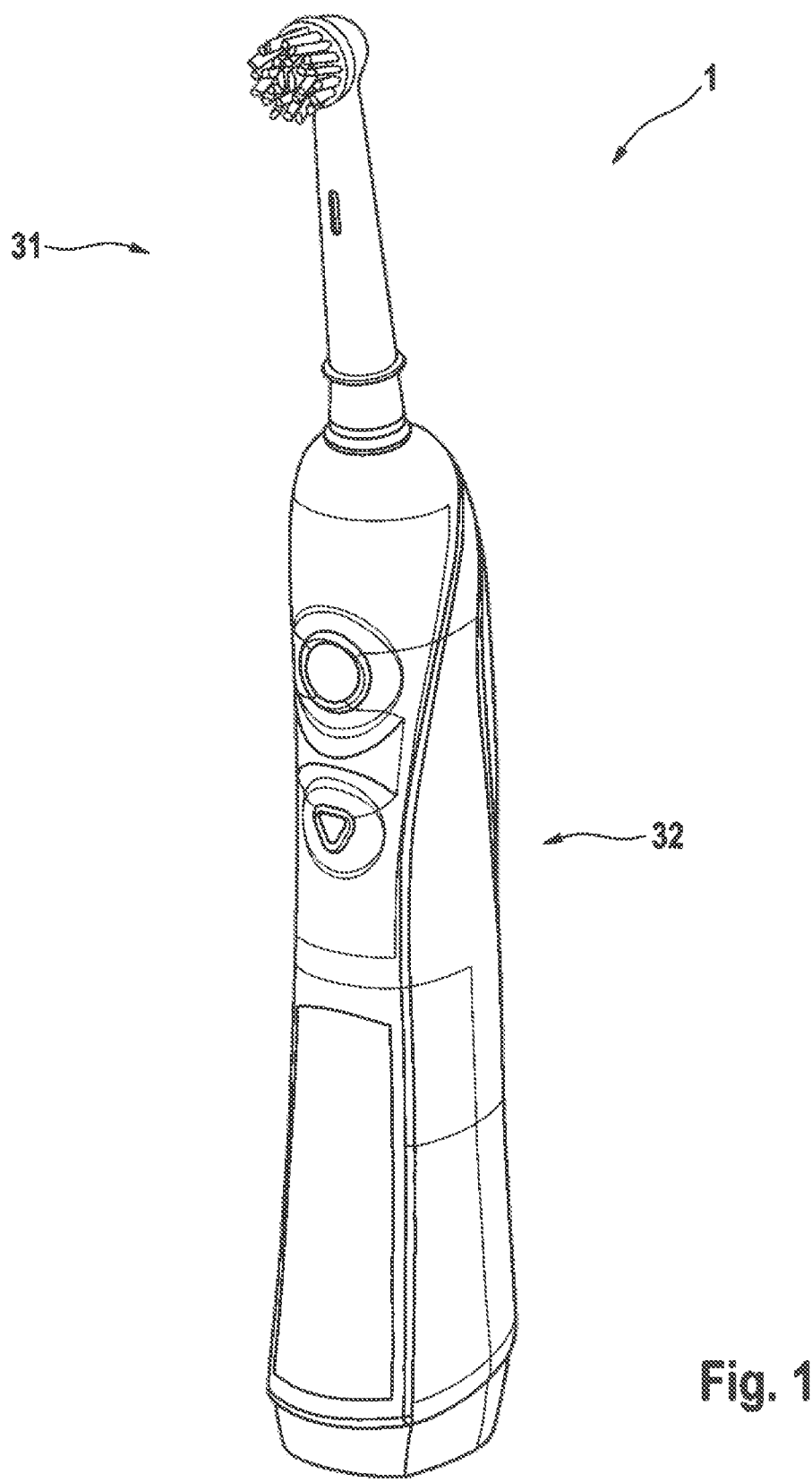
FIG. 1 shows an example oral hygiene device.

In accordance with the present description, an oral care implement as previously mentioned has a motion transmitter that comprises three parts, namely a first coupling part for connecting the motion transmitter with a carrier element, a second coupling part for connecting the motion transmitter with a drive shaft, and an elastic pivot element that connects the first coupling part and the second coupling part. The elastic pivot element allows pivoting of the first coupling part around a pivot point with respect to the second coupling part. In contrast to the previously mentioned known prior art implements, where a first part of a motion transmitter was itself pivotably coupled with a second part at a joint (the first part was pivotably supported in a bore provided at the second part), the here presented motion transmitter has no such mechanical connection that tends to suffer from mechanical tolerances and thus generates noise during operation. The elastic pivot element connects the first coupling part and the second coupling part and is itself an elongated element without mechanically interacting parts. It comprises in particular a hinge section, which may be realized as a living hinge (or: flexure bearing), i.e. a thin flexible hinge made in particular from the same material as the elastic pivot element. In particular, the elastic pivot element is realized as an injection molded plastic element. In some embodiments, the elastic pivot element has a first connecting portion that rigidly connects the first coupling part with the elastic pivot element and a second connecting portion that rigidly connects the second coupling part with the pivot element. In particular, the first coupling part and additionally or alternatively the second coupling part may be made from metal, either at least in those portions that are connected with the elastic pivot element or they may be made completely from metal. The first and/or the second coupling part may be connected with the elastic pivot part by means of a press fit, gluing, hot stamping, or a positive fit connection. The elastic pivot element has elastic properties allowing the elastic pivot element to repeatedly deform (flex) without breaking and thus allowing a pivoting movement of the first coupling part with respect to the second coupling part in at least a first pivoting plane. In some embodiments, the elastic pivot element is structured to allow also a defined pivoting motion of the first coupling part relative to the second coupling part in a second pivoting plane that is in particular perpendicular to the first pivoting plane. The material from which the elastic pivot element is made may have resilient properties that provide restoring forces acting to bring the elastic pivot element back into its rest position when it is deformed (flexed). The elastic pivot element (in particular its hinge section) is arranged so that pivoting in the first pivoting plane occurs with a restoring force that is in a range of between about 0.15 N·mm/degree to about 0.5 N·mm/degree and optionally where pivoting in a second pivoting plane perpendicular to the first pivoting plane occurs with a restoring force in a range of between about 2.5 N·mm/degree to about 4.0 N·mm/degree.

In case that the present disclosure defines a value for the Young's modulus of a material, such values are understood to have been measured in accordance with DIN EN ISO 527-1:2012 and DIN EN ISO 527-2:2012 at a room temperature of 23 degrees Celsius, at a relative humidity of 50%, and at a test velocity such that an expansion rate of 1% of the measurement length per minute is achieved (section 9.6 of DIN EN ISO 527-1: 2012). Where possible, measurements are to be performed with injection molded test specimens in accordance with test specimen type 1A (section 6.1 of DIN EN ISO 527-2:2012).

The elastic pivot element is made from a plastics material having a Young's modulus of not more than about 2000 MPa, optionally of not more than 1000 MPa, further optionally of not more than 500 MPa. In some embodiments, the Young's modulus of the plastics material forming the elastic pivot element is at least 100 MPa. Suitable materials include, but are not limited to polycarbonate (PC) having a Young's modulus of about 2400 MPa, polypropylene (PP) having a Young's modulus in the range of between 1300 MPA to 1800 MPa, polyethylene (PE) having a Young's modulus of about 1350 MPa (for PE-HD) down to 200 MPA (for PE-LD), or thermoplastic elastomers such as Hyrtel® from DuPont having a Young's modulus in the range of between 35 MPa to 1207 MPa depending on the Hyrtel® type. In contrast, at least the first coupling part is either made from a plastics material having a Young's modulus of at least about 5000 MPa (5 kN/mm$^2$), in particular of at least about 50 GPa, or the first coupling part may be made from a metal material such as stainless steel, brass, aluminum etc. Plastic materials with a high Young's modulus of above about 5000 MPa may in particular be realized by reinforced, e.g. glass fiber or carbon fiber reinforced plastic materials, e.g. PP reinforced with 30% glass fiber has a Young's modulus of about 7000 MPa and polyamide 6 reinforced with 50% glass fiber (PA 6 GF50; dry) has a Young's modulus of about 15000 MPa. Kern GmbH, Großmaischeid, Germany, offers a large variety of such reinforced plastic materials. Some carbon fibre reinforced plastic materials have a Young's modulus in the range of about 30 GPa to about 50 GPa. Metal materials such as steel or iron-based metals, brass, aluminum, bronze, titanium, copper etc. have a Young's modulus of above 50 GPa, in particular in the range of between about 70 GPa to about 200 GPa.

The particular structure of the motion transmitter as proposed allows for relatively energy-efficient motion transfer from a linearly oscillating drive shaft to a functional element, where the connection with the functional element is offset from the axis along which the drive shaft vibrates. In case the whole motion transmitter would be made from a suitably elastic material, too much energy would be absorbed by the deforming motion transmitter during operation. The proposed structure assures that mainly deformation happens in the elastic pivot element (in particular in a hinge section), which can be made relatively small. As the first (and second) coupling part(s) of the motion transmitter are made from a much less elastic material, much less deformation occurs in these parts.

The material from which the elastic pivot element is made also may have damping properties so that e.g. small amplitude high frequencies oscillations (e.g. vibrations) or shock waves are at least to some extent absorbed by the elastic pivot element and are not transferred from the first coupling part to the second coupling part or vice versa. At least some of the properties of the elastic pivot element as mentioned can be fulfilled by an elastic plastic material such as polypropylene or polyethylene (due to their good fatigue resistance) or a natural or artificial rubber, such as a thermoplastic elastomer (TPE) such as Hyrtel®. Besides fine tuning of the material with additives, the exact geometry of the elastic pivot element (in particular of a hinge section defining a pivot point) can as well be used to set the properties of the elastic pivot element as will be explained further below. The material from which the elastic pivot element is made may have a hardness in the range of about 40 Shore A to about 80 Shore D, in particular in a range of about 50 Shore A to about 65 Shore D.

The oral care implement in accordance with the present disclosure may in particular comprise a hollow housing at which the carrier element is mounted (e.g. by means of at least one axle for defining a movement axis and/or by means of a fixation element for connecting the carrier element with the housing, while allowing the intended driven movement). The motion transmitter would then at least partly be disposed within the hollow housing.

FIG. 1 is a depiction of an example oral hygiene device 1, here realized as an electric toothbrush. The oral hygiene device 1 generally comprises a head section 31 and a handle section 32. Here, the head section 31 is realized as a brush section that may in particular be attachable to and detachable from the handle section 32. The handle section 32 may comprise a drive with a drive shaft for transferring a driving motion to the head section 31. In accordance with the present disclosure, an oral hygiene implement may in particular be a replaceable head section of an oral hygiene device. In some embodiments, an oral hygiene implement is an oral hygiene device comprising a head section and a handle section (where the head section may not be replaceable even though this shall not be excluded), the handle section may comprise a drive and a drive shaft.

Instead of being realized as an electric toothbrush, an oral hygiene device or oral hygiene implement may also be realized as a flossing device, a gum massage device, an interdental cleaning device etc. In accordance with the present disclosure, an oral hygiene implement may alternatively be realized as a (in particular detachable) head section of a flossing device, gum massaging device, interdental cleaning device etc.

Figure 2:
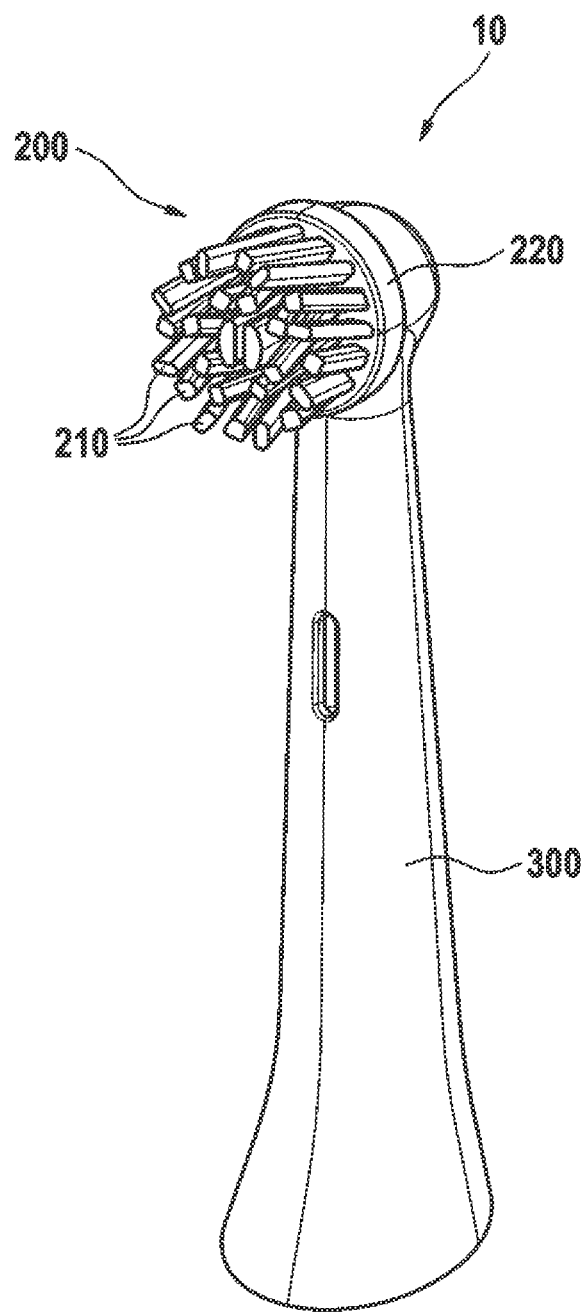
FIG. 2 is a depiction of an example oral hygiene implement.

FIG. 2 is a perspective view onto an example oral hygiene implement 10, here realized as a replacement brush head for detachable attachment to a handle section of an oral hygiene device. The oral hygiene implement 10 has a head 200 that comprises a carrier element 220 on which cleaning elements 210 such as bristle tufts or elastomeric elements are mounted. The carrier element 220 is mounted at a housing 300 of the oral hygiene implement 10 for driven movement. The housing may in particular be hollow.

Figure 3:
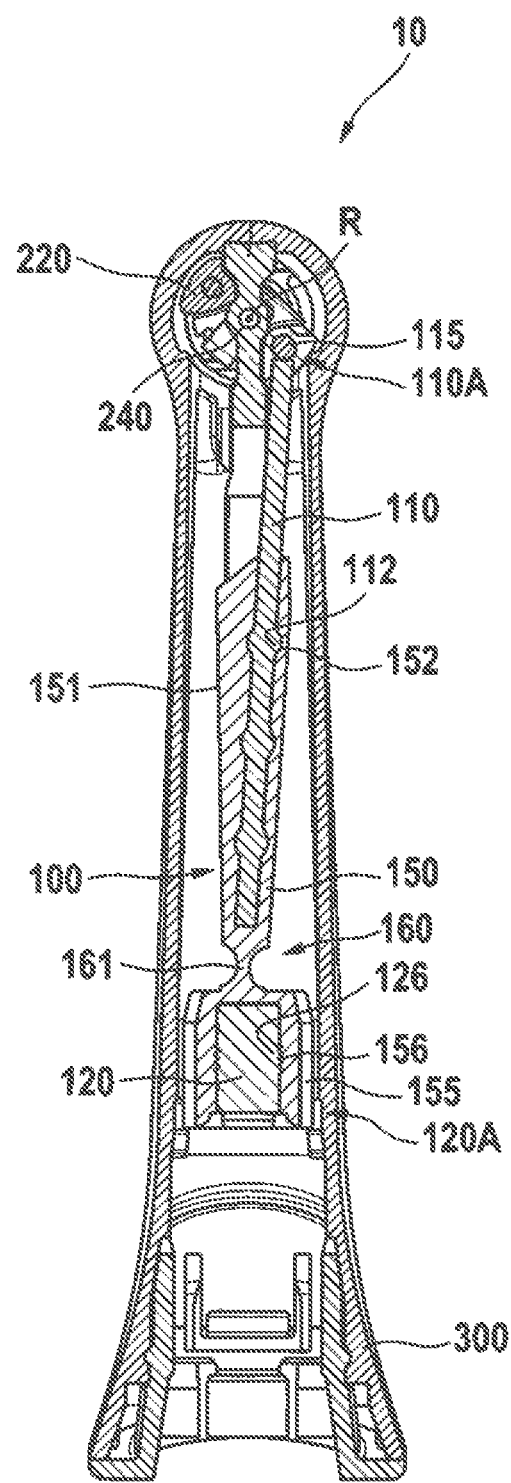
FIG. 3 is a depiction of a cut-open oral hygiene implement comprising a motion transmitter.

FIG. 3 is a depiction of the oral hygiene implement 10 shown in FIG. 2 cut open so that a motion transmitter 100 is visible that is on a first end 110A connected to the carrier element 220 and that has a second end 120A provided for connection with a drive shaft from a handle section of an oral hygiene device. The housing 300 is hollow and the motion transmitter 100 is disposed within the hollow of the housing 300 (even though in some embodiments, a part of the motion transmitter extends beyond the lower edge of the hollow housing).

Figure 4A:
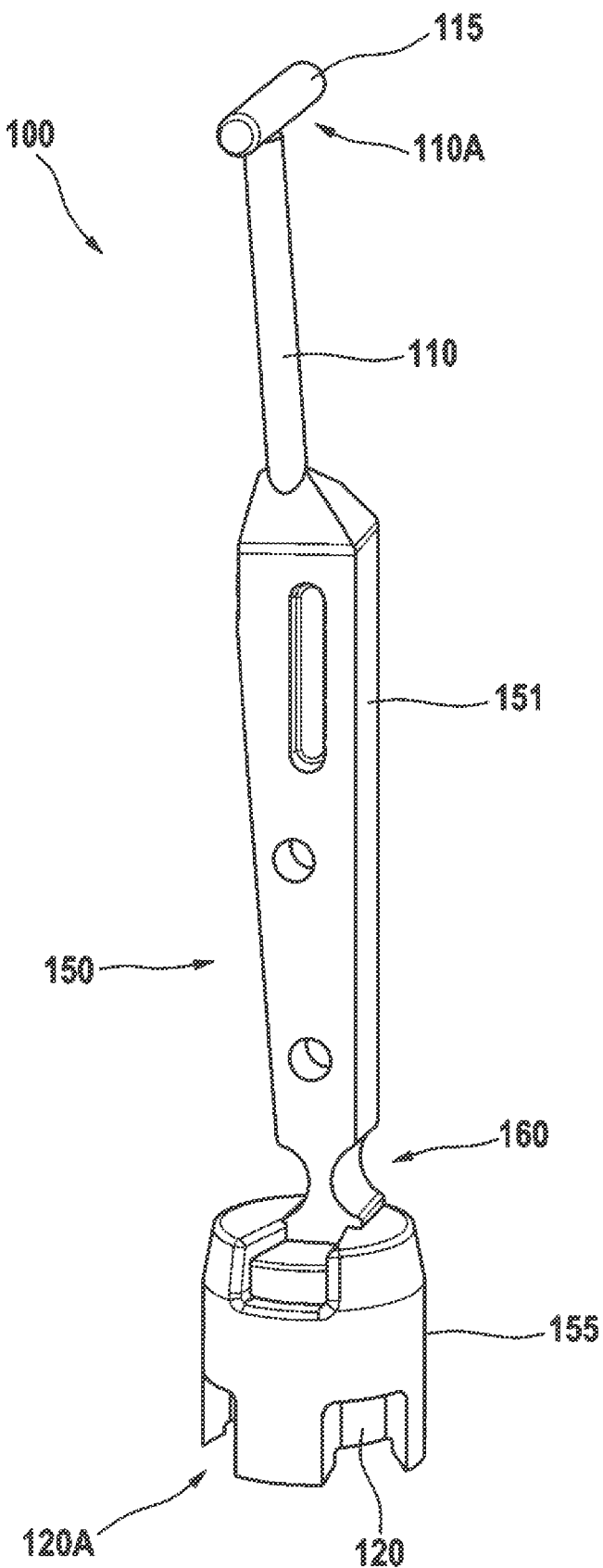
FIG. 4A is a perspective depiction of the motion transmitter shown in FIG. 3.
Figure 4B:
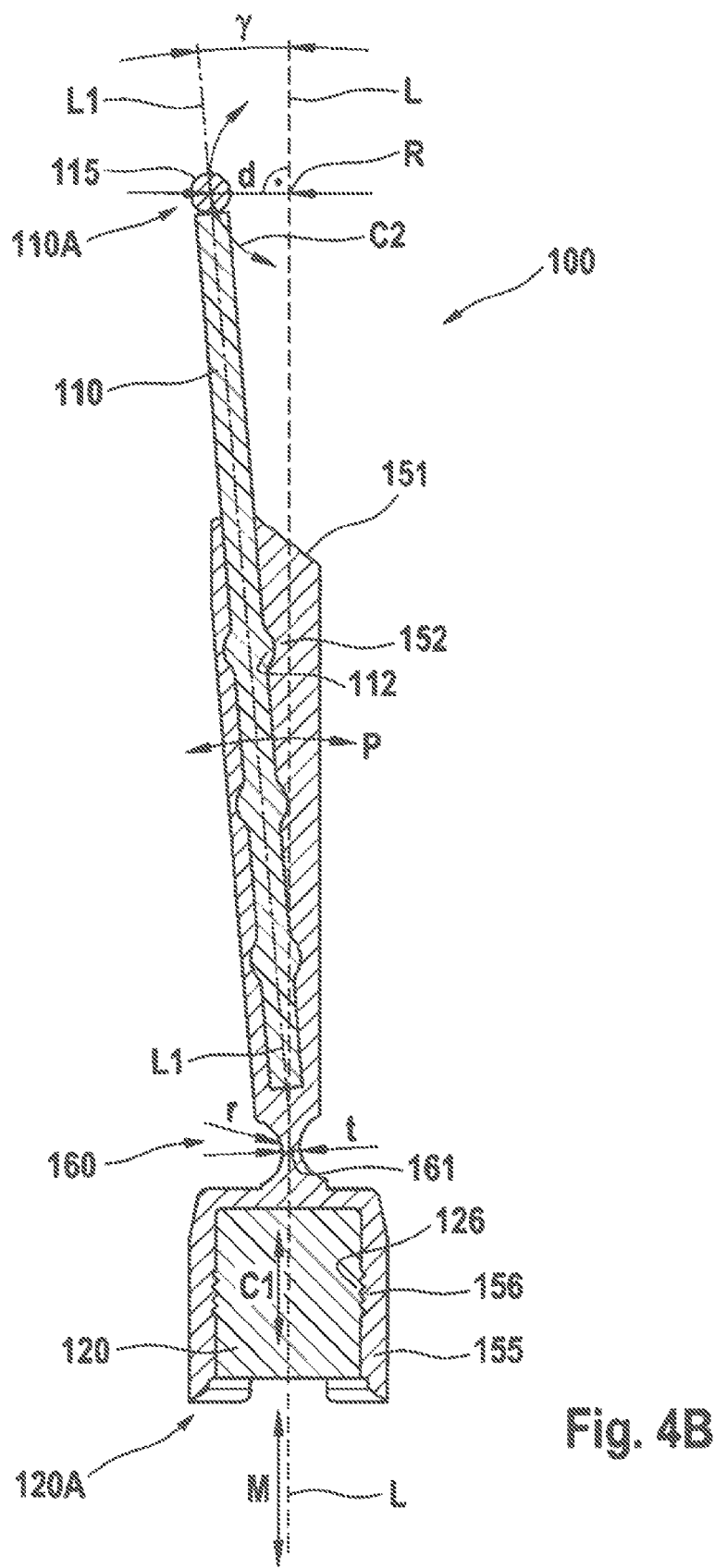
FIG. 4B is a cross-sectional cut through the motion transmitter shown in FIG. 4A.

FIG. 4A is a perspective view onto the isolated motion transmitter 100 shown in FIG. 3. FIG. 4B is a longitudinal cut through the motion transmitter 100 of FIG. 4A.

In the following, reference is made to FIGS. 3, 4A, and 4B when the motion transmitter 100 is discussed and to FIG. 3 when the oral care implement 10 and arrangement of the motion transmitter 100 within the oral care implement 10 is discussed.

The motion transmitter 100 comprises a first coupling part 110 and a second coupling part 120 that are connected by an elastic pivot element 150 that allows that the first and the second coupling part 110, 120 can pivot with respect to each other at least within a first pivoting plane. That means that the first and second coupling parts can be made from materials having a relatively high Young's modulus as the deformation capability is provided by the elastic pivot element. This pivoting is allowed as the elastic pivot element 150 will elastically deform (or: deflect) under an applied force acting e.g. at the first end 110A of the motion transmitter 100. In some embodiments, the first coupling part 110 is at least partly made from metal such as stainless steel, brass, aluminum etc. In the shown embodiment, the second coupling part is made at least partly from a permanent magnetic material such as an Al—Ni—Co material or a Nd—Fe—B material or a magnetizable material such as iron, cobalt, or nickel (even though this shall not exclude that the second coupling part 120 is also made from steel, aluminum, brass etc.). The elastic pivot element 150 is made from a material that allows that the first coupling part 110 and the second coupling part 120 can pivot with respect to each other around a pivot point 161 (at least for a certain angular range such as up to ±1 degrees, ±5 degrees or up to a ±10 degrees or up to ±15 degrees etc. around a centre position). A suitable material may be an elastic plastics material such as polypropylene or polyethylene or an elastomeric material such as a thermoplastic elastomer (TPE) or a natural rubber as has been discussed in a previous paragraph. The elastic pivot element 150 may in particular have a hinge section 160 that in some embodiments forms a living hinge. While a living hinge may not be a necessary structure, a living hinge can be finely tuned in its geometric dimensions (in addition to the material choice) so that certain characteristics as the return force properties of the pivot element under flexing can be set as is explained further below. Generally, the elastic pivot element 150 or at least the hinge section 160 may be made from a material having a hardness in the range of about 40 Shore A to about 80 Shore D, in particular the hardness may lie in a range of about 50 Shore A to about 65 Shore D. Polypropylene and polyethylene materials typically have a Shore D hardness in the range of between about 55 Shore D to about 75 Shore D. Medium soft or harder rubber or TPE materials suitable for the hinge section have a hardness of about 40 Shore A or higher (up to typically about 95 Shore A, which is equivalent to about 45 Shore D). It had been found that one suitable material for forming the elastic pivot element is Hyrtel® 6359 FG NC010 from DuPont, Wilmington, Del., USA. Hyrtel® is a family of thermoplastic elastomer materials with good durability characteristics. The mentioned Hyrtel® variety has a Young's modulus of 260 MPa and Shore D hardness (max) of 63. Hyrtel® 6359 FG NC010 thus has a Young's modulus that is higher than the respective value for typical rubber materials (lying in the range of about 10 MPa to about 100 MPa) but that is also considerable lower than that of some elastic plastic materials (e.g. some PP types have a Young's modulus of about 1300 to about 1800 MPa) and similar to a low density PE (having a value in the range of about 110 to about 450 MPA).

Generally, the first coupling part 110 comprises the first end 110A of the motion transmitter 100 for connection with a carrier element 220. In the shown embodiment, a connector element 115 (here realized as a short rod element that is a welded portion of the first coupling part 110 here realized as a long rod element such that a T-like structure is formed) is provided at the first end 110A of the motion transmitter 100, which rod element 115 extends into a bore of the carrier element 220, which bore is arranged eccentrically with respect to an axle 240 that defines the motion axis R of the carrier element 220 when being driven. The second coupling part 120 comprises the second end 120A of the motion transmitter 100 intended for coupling with a drive shaft of a handle of an oral hygiene device as was also previously mentioned. In the shown embodiment, the coupling between the second end and the drive shaft is intended to be a magnetic coupling (European patent application 12177800.5, the relevant content of which is included herein by reference, describes such a magnetic coupling). The second coupling part 120 may then be realized as a magnetizable element that is e.g. made from iron and the coupling partner on the drive shaft may then be realized as a permanent magnet, e.g. made from a NdFeB (Neodymium) material. In some embodiments, the second end may be arranged for a mechanical coupling, e.g. by means of snap partners (spring latch partners), where the second end is provided with one mechanical coupling partner and the drive shaft is equipped with the respective complementary coupling partner.

The elastic pivot element 150 connects the first coupling part 110 and the second coupling part 120 and allows that those two coupling parts can pivot with respect to each other around a pivot point 161. The elastic pivot element 150 comprises a first connecting portion 151 rigidly connecting the elastic pivot element 150 with the first part 110 of the motion transmitter 100 and a second connecting portion 155 rigidly connecting the elastic pivot element 150 with the second coupling part 120 of the motion transmitter 100. The elastic pivot element 150 here also comprises a hinge portion 160 that may be realized as a living hinge so that the first coupling part 110 can pivot with respect to the second coupling part 120 around a pivot point 161 as indicated by double arrow P in FIG. 4B. As can also in particular be seen in FIG. 4B, a centre axis L1 of the first coupling part 110 is arranged in a rest position at an angle y with respect to the longitudinal axis L of the oral hygiene implement. The longitudinal axis L of the oral hygiene implement 10 is here coinciding with the axis along which the drive shaft of the handle section oscillates (as indicated by double arrow M). Thus, when being driven, the drive shaft provides an oscillating motion M along longitudinal axis L, which causes the second coupling part 120 of the motion transmitter to follow this motion M due to its in particular magnetic or mechanical coupling with the drive shaft and to move in an oscillatory manner along a path C1 lying on the longitudinal axis L. The movement of the first part 110 is then constrained and defined by the first end 110A of the first coupling part 110 being mounted eccentrically at the carrier element 220 (the connector element 115 is here mounted at a distance d to the rotation axis R, which rotation axis R crosses the longitudinal axis L), which carrier element 220 itself can only rotate (or oscillate) around rotation axis R. Thus, the first end 110A (here: the connector element 115) must move along an arc around the rotation axis R as indicated by double arrow C2. During this movement along the arc C2, the first coupling part 110 pivots with respect to second coupling part 120 around the pivot point 161 defined by the hinge section 160.

In some embodiments, the elastic pivot element 150 is an injection molded part. The first coupling part 110 and the second coupling part 120 may be provided in a mold having a mold cavity into which a plastic material will be injected for forming the pivot element. In order to fixedly connect the first coupling part 110 and/or the second coupling part 120 with the injection molded elastic pivot element 150, the first coupling part 110 and/or the second coupling part 120 may each comprise at least one undercut section 112 and/or 126 that may comprise a recess, cutout, through-hole, indentation, protuberance, or projection so that a positive fit between the first coupling part 110 and/or the second coupling part 120 and the material of the elastic pivot element 150 is formed so that the first coupling part 110 and/or the second coupling part 120 cannot be separated from the elastic pivot element 150 without damaging the motion transmitter 100. Such a solution is in particular suitable if the material of the first coupling part 110 and/or second coupling part 120 does not form a chemical bond with the material of the elastic pivot element 150 during the injection molding process.

In some embodiments, the first coupling part 110 has at least one undercut section 112 and the first connecting portion 151 of the elastic pivot element 150 has at least one undercut section 152 that is a negative of the undercut section 112 so that they together form a positive fit connection for rigidly connecting the first coupling part 110 and the elastic pivot element 150. Similarly, in some embodiments, the second coupling part 120 has at least one undercut section 126 and the second connecting portion 155 has at least one undercut section 156 that is a negative the undercut section 126 so that they together form a positive fit connection for rigidly connecting the second coupling part 120 and the elastic pivot element 150. In some embodiments, the first coupling part 110 may comprise a metal (e.g. steel) rod element and the at least one undercut section 112 may be formed by stamping or by another mechanical or chemical treatment of the rod element. In some embodiments, the first or second coupling part may receive an undercut section during the manufacture of the respective first or second coupling part, e.g. the first or second coupling part may be made as a sintered or cast or injection molded element. The mentioned undercut section(s) may comprise at least one or more of a recess, a cut-out, a through-hole, an indentation, a protuberance, or a projection.

In simulations it had been found that a suitable return force when pivoting (i.e. deflecting) the first coupling part with respect to the second coupling part should be in a range of between about 0.15 N·mm/degree of deflection to about 0.5 N·mm/degree of deflection. The deflection force is depending on material properties of the hinge section 160 such as the Young's modulus of the material from which the hinge section 160 is made, the minimum material thickness t of the hinge section 160 and the radius r of the minimum thickness part of the hinge section 160. If the living hinge section shown in FIG. 4B were made of Hyrtel® 6359 FG NC010 as mentioned before, it had been found that the thickness t should be in a range of between about 0.5 mm to about 0.75 mm and that the radius r should be in a range of between about 1.0 mm to about 2.0 mm.

In addition to the above, the elastic pivot element may also allow for a pivoting motion of the first coupling part 110 relative to the second coupling part 120 in a second pivoting plane perpendicular to the first pivoting plane, which first pivoting plane is the drawing plane of FIG. 4B. If the drawing plane would be spanned by an x axis perpendicular to the longitudinal axis L and an y axis coinciding with the longitudinal axis L and both axes crossing each other in the pivot point 161, the second pivoting plane would then be spanned by the centre axis L1 of the first coupling part and an xl axis being perpendicular to the centre axis L1 and crossing the pivot point 161. Such added flexibility of the motion transmitter tends to balance misalignment between the various parts of the motion transmitter, the carrier element and the drive shaft and as a result, wear of the components is effectively reduced. Numerical simulations have shown, that the pivoting in the second pivoting plane may occur under a restoring force of between about 2.5 N·mm/degree and about 4.0 N·mm/degree. Generally, the ratio between the restoring forces provided in the second pivoting plane and the restoring forces in the first pivoting plane may be in a range of between about 5 and about 30.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral hygiene implement having
   a longitudinal axis;
   a carrier element mounted for driven movement;
   a motion transmitter that has a first end for transferring a drive force to the carrier element, which first end is provided at a position being offset from the longitudinal axis, and the motion transmitter has a second end positioned essentially on the longitudinal axis or is arranged for being positioned essentially on the longitudinal axis during operation;
   wherein the motion transmitter has a first coupling part comprising the first end, which first coupling part essentially extends along a centre axis arranged at an angle with respect to the longitudinal axis, and a second coupling part comprising the second end, which first coupling part is fixedly connected with a first connecting portion of an elastic pivot element that allows that the first coupling part and the second coupling part can pivot with respect to each other at least in a first pivoting plane spanned by the longitudinal axis and by the centre axis, wherein the elastic pivot element is arranged so that pivoting in the first pivoting plane occurs with a restoring force in a range of between about 0.15 N·mm/degree and about 0.5 N·mm/degree; and
   wherein the first coupling part is made from a plastics material, including reinforced plastics materials, having a Young's modulus of at least 5000 MPa or from a metal material, and at least the first connecting portion is made from a plastics material having a Young's modulus of not more than 3000 Mpa.

2. The oral hygiene implement in accordance with claim 1, wherein the elastic pivot element is an injection molded elastic pivot element.

3. The oral hygiene implement in accordance with claim 1, wherein the first coupling part of the motion transmitter is made from a metal material.

4. The oral hygiene implement in accordance with claim 1, wherein the second coupling part is fixedly connected with a second connecting portion of the elastic pivot element.

5. The oral hygiene implement in accordance with claim 1, wherein the first coupling part comprises an undercut section comprising a recess, cut-out, through-hole, indentation, protuberance, or projection that is in a positive fit connection with the first connecting portion of the elastic pivot element.

6. The oral hygiene implement in accordance with claim 1, wherein the elastic pivot element comprises a hinge section that defines a pivot point about which the first coupling part and the second coupling part can pivot, in particular where the hinge section is formed as a living hinge.

7. The oral hygiene implement in accordance with claim 6, wherein at least the living hinge of the elastic pivot element is made from a non-elastomeric plastic material such as polypropylene or polyethylene.

8. The oral hygiene implement in accordance with claim 6, wherein at least the living hinge of the elastic pivot element is made from a thermoplastic elastomer.

9. The oral hygiene implement in accordance with claim 1, wherein the elastic pivot element is made from a material having a hardness in the range of from about 40 Shore A to about 80 Shore D.

10. The oral hygiene implement in accordance with claim 1, wherein pivoting in a second pivoting plane perpendicular to the first pivoting plane occurs with a restoring force in a range of between about 2.5 N·mm/degree and about 4.0 N·mm/degree.

11. The oral hygiene implement in accordance with claim 1, wherein the first end of the motion transmitter is arranged to move along a line inclined with respect to the longitudinal axis or on a curve with respect to the longitudinal axis and the second end of the motion transmitter is arranged for movement essentially along the longitudinal axis.

12. The oral hygiene implement in accordance with claim 1, further comprising a hollow housing and wherein the motion transmitter is disposed within the hollow housing.

13. The oral hygiene implement in accordance with claim 1, wherein the motion transmitter is at the second end connected to or connectable with a drive shaft of a handle portion.

14. The oral hygiene implement in accordance with claim 1, wherein the oral hygiene implement is realized as a replacement part, in particular a replacement brush head, attachable to and detachable from a handle portion of an oral hygiene device.

15. The oral hygiene implement in accordance with claim 1, wherein the oral hygiene implement is realized as an oral hygiene device comprising a drive having a drive shaft that is connected with the motion transmitter.

16. The oral hygiene implement in accordance with claim 1, wherein the elastic pivot element is made from a plastic material having a Young's modulus of not more than 1000 Mpa.

17. The oral hygiene implement in accordance with claim 1, wherein the elastic pivot element is made from a plastic material having a Young's modulus of not more than 500 Mpa.

18. The oral hygiene implement in accordance with claim 1, wherein the elastic pivot element is made from a material having a hardness in the range of from about 50 Shore A to about 65 Shore D.

19. An oral hygiene implement having
a longitudinal axis;
a carrier element mounted for driven movement;
a motion transmitter that has a first end for transferring a drive force to the carrier element, which first end is provided at a position being offset from the longitudinal axis, and the motion transmitter has a second end positioned essentially on the longitudinal axis or is arranged for being positioned essentially on the longitudinal axis during operation;
wherein the motion transmitter has a first coupling part comprising the first end, which first coupling part essentially extends along a centre axis arranged at an angle with respect to the longitudinal axis, and a second coupling part comprising the second end, which first coupling part is fixedly connected with a first connecting portion of an elastic pivot element that allows that the first coupling part and the second coupling part can pivot with respect to each other at least in a first pivoting plane spanned by the longitudinal axis and by the centre axis; and
wherein the first end of the motion transmitter is arranged to move along a line inclined with respect to the longitudinal axis or on a curve with respect to the longitudinal axis and the second end of the motion transmitter is arranged for movement essentially along the longitudinal axis.

20. The oral hygiene implement in accordance with claim 19, wherein the first coupling part is made from a plastic material having a Young's modulus of at least 5000 MPa or from a metal material, and the first connecting portion is made from a plastic material having a Young's modulus of not more than 3000 Mpa.

* * * * *